US00PP25801P2

(12) United States Plant Patent
Osiecki

(10) Patent No.: US PP25,801 P2
(45) Date of Patent: Aug. 11, 2015

(54) ***ALOCASIA* PLANT NAMED 'ALO2'**

(50) Latin Name: ***Alocasia* hybrid**
Varietal Denomination: ALO2

(71) Applicant: Marian Osiecki, Marianna, FL (US)

(72) Inventor: Marian Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 159 days.

(21) Appl. No.: 13/986,614

(22) Filed: May 16, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Alocasia* cultivar named 'ALO2' is disclosed, characterized by dark green, glossy foliage with veins surrounded by silver shadows. Plants are very vigorous, forming many basal shoots, symmetrical in form and suitable for production in commercial 6 or 8 inches pots from a single tissue culture plantlet. The new variety has closely overlapping cordate leaf blades and thick, contrasting light pink petioles with green streaks. The new variety is very easy to grow under low and high light conditions and well as low and high temperature conditions. The new variety also has exceptionally long 6 month shelf life. The new variety is an *Alocasia*, typically produced as an ornamental plant.

1 Drawing Sheet

Latin name of the genus and species: *Alocasia* hybrid.
Variety denomination: 'ALO2'.

BACKGROUND OF THE INVENTION

The new cultivar is a product of a planned breeding program. The objectives of the planned breeding program were to develop new *Alocasia* varieties of small to medium size, with rapid, vigorous growth, early and strong basal branching as well as columnar growth, suitable for 6-8 inch commercial pot production. The inventor additionally sought new varieties with interestingly ornamental foliage, and colorful, strongly contrasting leaf peduncles and long shelf life. The new variety originated from a cross pollination of an unpatented seed parent referred to as 'Aurora' and the pollen parent, the unpatented, variety of *Alocasia* known as 'Polly'. The crossing was made during May of 2007.

The new variety was discovered by the inventor, Marian Osiecki, a citizen of the US, in October of 2008 in a group of seedlings resulting from the crossing. The new cultivar was found in a commercial greenhouse in Altha, Fla.

Asexual reproduction of the new cultivar 'ALO2' was first performed at a commercial laboratory in Altha, Fla. by tissue culture on Mar. 3, 2009. Subsequent propagation by tissue culture has shown that the unique features of this cultivar are stable and reproduced true to type.

SUMMARY OF THE INVENTION

The cultivar 'ALO2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALO2'. These characteristics in combination distinguish 'ALO2' as a new and distinct *Alocasia* cultivar:

1. Small to medium size, very vigorous, fast growing plant with strong basal shoot production.
2. Symmetrical growth habit.
3. Dark green, very thick, glossy foliage with veins surrounded by silver shadow.
4. Close overlapping, cordate shaped leaf blades.
5. Attractive, very strong, thick, pink petioles with well marked green or brown streaks.
6. Very easy to grow even under low or high light levels, as well in low or high temperatures.
7. Exceptionally long 6 months shelf life.
8. 'ALO2' is suitable for production in 6-8" pots from a single tissue culture micro cutting plantlet.
9. Strong plant, tolerates stressful conditions.

PARENT COMPARISON

Plants of the new cultivar 'ALO2' are similar to the unpatented seed parent 'Aurora' in most horticultural characteristics. The new variety however differs in the following characteristics:

1. 'ALO2' is a more vigorous and faster growing plant than 'Aurora'.
2. 'ALO2' is a shorter plant, in a 6" pot it is 25-30 cm tall, whereas 'Aurora' is 50-60 cm tall.
3. Plants of 'ALO2' have a more symmetrical growth form and are narrower in diameter compared to 'Aurora'.
4. Plants of 'ALO2' are less spreading, less open in form compared to 'Aurora'.
5. The leaf blades of 'ALO2' are smaller, darker green, thicker and glossier compared to the larger, thinner, light green leaf blades of 'Aurora'.
6. Leaf veins of 'ALO2' are thicker, having a darker and broader silver shadow than 'Aurora'.

7. The lower side of 'ALO2' leaf blade of is glossy, burgundy with some green area, whereas the lower side of 'Aurora' leaf blade of is green and matte.
8. Leaf petioles of 'ALO2' are shorter, thicker and much stronger compared to petioles of 'Aurora'.
9. Leaf petioles of 'ALO2' are pink with well marked green streaks where leaf petioles of 'Aurora' are darker pink with very delicate green streaks.
10. 'ALO2' is a stronger plant, has a longer shelf life, it is more tolerant to disease and stress conditions than 'Aurora'.

Plants of the new cultivar 'ALO2' are similar to the pollen parent, an unpatented, variety of *Alocasia* known as 'Polly' in most horticultural characteristics. The new variety however differs in the following characteristics:

1. 'ALO2' is a more vigorous, taller and faster growing plant than 'Polly'.
2. 'ALO2' makes basal shoots earlier and more abundantly than 'Polly'.
3. 'ALO2' is fuller, less spreading and less open than 'Polly'.
4. Leaf blades of 'ALO2' are thicker, bigger, slightly lighter in color, less glossy and have less silver color between veins compared to smaller leaves of 'Polly'.
5. Leaf veins of 'ALO2' have narrower silver shadow than 'Polly'.
6. 'ALO2' leaf petioles are pink with well marked green streaks, whereas 'Polly' leaf petioles are light green to green color with a few very light green streaks.
7. 'ALO2' is more tolerant to disease and stress conditions than 'Polly'.

COMMERCIAL COMPARISON

'ALO2' can be compared to the unpatented species *Alocasia amazonica*. Plants of *Alocasia amazonica* are similar to plants of 'ALO1' in most horticultural characteristics. However 'ALO2' differs from *Alocasia amazonica* in the following characteristics:

1. 'ALO2' is a more vigorous and faster growing plant than *A. amazonica.*
2. 'ALO2' is a fuller plant, makes basal shoots earlier and more abundantly compared to *A. amazonica.*
3. Plants of 'ALO2' are shorter, less spreading, and less open compared to *A. amazonica.*
4. Plants of 'ALO2' are much more symmetrical and narrower in diameter compared to *A. amazonica.*
5. The leaf blades of 'ALO2' are thicker, much smaller, with less silver color between veins compared to *A. amazonica.*
6. Leaf veins of 'ALO2' are surrounded by a narrower silver shadow compared to *A. amazonica.*
7. The lower side of 'ALO2' leaf blade is burgundy with some green area, whereas the lower side of *A. amazonica* leaf blade is dark burgundy.
8. The leaf margins of 'ALO2' are green-silver and undulate whereas the leaf margins of *A. amazonica* are bright silver and lobed.
9. Leaf petioles of 'ALO2' are pink with well marked green streaks whereas the leaf petioles of *A. amazonica* are light green to green color without visible streaks.
10. 'ALO2' is a stronger plant, has longer shelf life, and better tolerates disease and stress conditions than *A. amazonica.*
11. Leaves of 'ALO2' closely overlap each other whereas leaves of *A. amazonica* are spread.

'ALO2' can be compared to the commercial variety *Alocasia* 'ALO3' application Ser. No. 13/986,615. Plants of 'ALO3' are similar to plants of 'ALO2' in most horticultural characteristics. However 'ALO2' differs from 'ALO3' in the following characteristics:

1. Plants of 'ALO2' are shorter than plants of 'ALO3'. Typically plants of 'ALO2' grow to 45 cm in height, whereas similar aged plants of 'ALO3' are 60 cm tall.
2. Upper foliage of 'ALO2' has a glossy appearance whereas 'ALO3' has an upper surface which is matte to leathery in appearance.
3. The petiole of 'ALO2' is shorter, typically 25 to 35 cm; the petiole of 'ALO3' ranges from 35 to 45 cm

BRIEF DESCRIPTION OF THE PHOTOGRAPH

The accompanying photograph in FIG. 1 illustrates in full color a typical plant of 'ALO2' grown in a greenhouse in Altha, Fla. This plant is approximately 6 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'ALO2' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Plants were grown in 80% shade, resulting in approximately 800 to 1200 foot candles of light. Measurements and numerical values represent averages of typical plant types.

Botanical classification: *Alocasia* hybrid 'ALO2'.

PROPAGATION

Root description: Thick, fleshy roots. Roots approximately 0.6 cm thick, colored near RHS White 155A. Rhizomes observed: Approximately 1 cm thick, colored RHS Greyed-Red 180D and RHS Greyed-Red 179C, both colors present.

PLANT

Growth habit: Rapid, upright. Basal leaves emerge in clumps.
Plant shape: Upright, petioles and leaves slightly arching out. No stems.
Height: Approximately 50 cm to top of foliar plane.
Plant spread: Approximately 45 cm in a 6 inch pot.
Pot size of plant described: 6 inch.
Growth rate: Rapid, vigorous.
Branching characteristics: No true branching. Leaves emerge direct from base of plant.
Number of clumps of leaves: 3.
Number of leaves per clump: Average 4 to 8.
Number of leaves per plant: Approximately 10 to 30.
Age of plant described: Approximately 6 months.

FOLIAGE

Leaf:

*Arrangement*.—Single leaves emerging basally.

*Largest, mature, fully expanded leaf*.—Length (excluding petiole): Range from 33 to 48 cm. Width: Range from 17 to 22 cm. Shape of blade: Cordate, with two very deep lobes that angle toward each other with age. Oldest leaves have lobes that slightly overlap. Aspect: Slightly undulating, mainly flat. Puckered. Apex: Apiculate Base: Cordate, with 2 very deep lobes. Margin: Entire. Appearance: Upper surface glossy. Lower surface glossy. Texture of top surface: Smooth, puckered. Texture of bottom surface: Smooth, puckered. Color: Mature foliage upper side: Near RHS Greyed-Green N189A. Mature foliage under side: Background color RHS Green 137B, heavily flushed RHS Greyed-Purple 187A.

Venation:

*Type*.—Pinnate.

*Venation coloration upper side*.—Outermost veins near RHS Greyed-Green 192C, secondary veins near RHS Greyed-Green 193A. Center vein, RHS Green 137C.

*Venation coloration under side*.—Near RHS Greyed-Purple 187A.

Petiole:

*Length*.—Approximate range between 25 and 35 cm.

*Width*.—At base: Approximately 1.5 cm. At leaf attachment: Approximately 0.6 cm.

*Color*.—Near RHS Greyed-Red 182C, moderately covered in short stripes near RHS Brown 200B and Yellow-Green 147A. Near leaf attachment, color changes to RHS Yellow-Green 145C, with stripes becoming less frequent, then absent approximately 1 cm from attachment point.

*Strength*.—Very strong.

*Texture*.—Glabrous.

*Other*.—Petiole sheath present.

Petiole sheath:

*Length*.—Approximately 7.0 cm.

*Width*.—Approximately 3.2 cm.

*Shape*.—Deltoid.

*Color*.—Near RHS Greyed-Red 182D, moderately covered in short stripes near RHS Brown 200B.

*Texture*.—Glabrous.

Immature foliage:

*Length* (*excluding petiole*).—Range from 10 to 18 cm.

*Width*.—Range from 5 to 9 cm.

*Shape of blade*.—Cordate, with two very deep lobes, youngest leaves less deeply lobed.

*Aspect*.—Slightly undulating, mainly flat. Puckered.

*Apex*.—Apiculate.

*Base*.—Cordate, with 2 very deep lobes.

*Margin*.—Entire.

*Appearance*.—Young foliage upper surface glossy, lower surface somewhat glossy.

*Texture of top surface*.—Smooth.

*Texture of bottom surface*.—Smooth.

*Color*.—Young foliage upper side: Near RHS Greyed-Green N189A. Young foliage under side: Near RHS Greyed-Purple N186A.

Immature foliage venation:

*Type*.—Pinnate.

*Venation coloration upper side*.—Near RHS Greyed-Green 191C.

*Venation coloration under side*.—Near RHS Greyed-Purple N186A.

INFLORESCENCE

Not observed to date.

OTHER CHARACTERISTICS

Disease resistance: Greater resistance than typical of *Alocasia* to *Myrothecium* and leaf *Phytophthora* has been observed.

Drought tolerance and cold tolerance: The new cultivar is a typical *Alocasia*, cold tolerant to approximately 5° to 7° C. and does not tolerate drought.

Fruit/seed production: Not observed.

What is claimed is:

1. A new and distinct cultivar of *Alocasia* plant named 'ALO2' as herein illustrated and described.

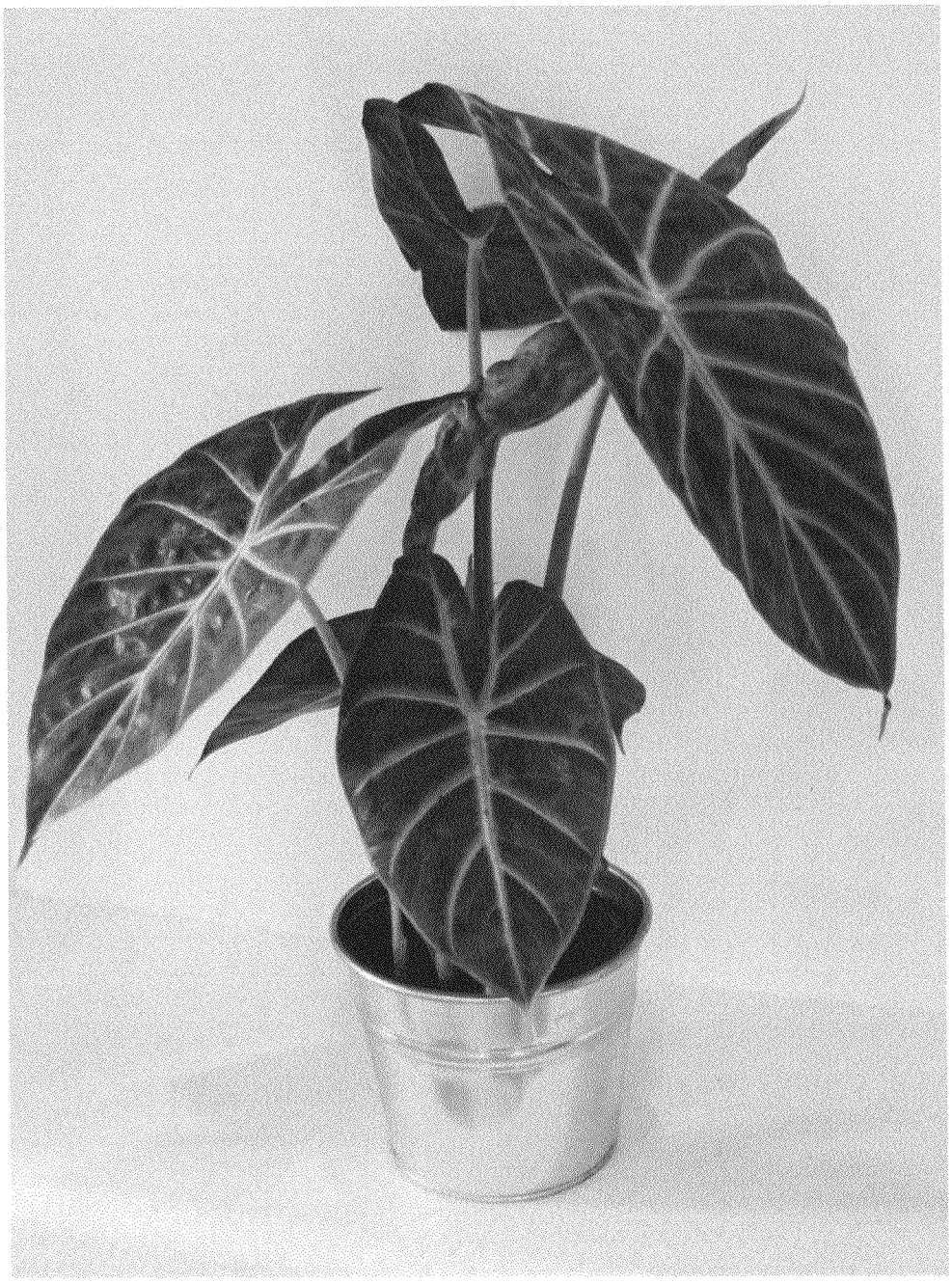

* * * * *